United States Patent

Tarutani et al.

[11] Patent Number: 5,882,378
[45] Date of Patent: Mar. 16, 1999

[54] METHOD TO DETECT METAL IMPURITIES IN THE SEMICONDUCTOR PROCESS GASES

[75] Inventors: Kohei Tarutani; Itsuko Suzuki, both of Tsukuba, Japan

[73] Assignee: L'Air Liquide Societe Anonyme Pour L'Etude et L'Exploitation des Procedes Georges Claude

[21] Appl. No.: 900,190

[22] Filed: Jul. 25, 1997

[51] Int. Cl.⁶ .................................................. B01D 47/02
[52] U.S. Cl. ..................... 95/8; 55/385.2; 95/226; 96/351; 96/413; 96/417
[58] Field of Search .......................... 95/8, 226; 55/385.1, 55/355.2, 244, 256, 270; 96/329, 330, 351, 413, 417, 166, 146, 134

[56] References Cited

U.S. PATENT DOCUMENTS

| | | | |
|---|---|---|---|
| 1,740,462 | 12/1929 | Hutton | 95/226 |
| 4,723,967 | 2/1988 | Tom | 55/256 |
| 4,883,505 | 11/1989 | Lucero | 55/270 |
| 4,892,568 | 1/1990 | Prigge et al. | 95/226 |
| 4,936,877 | 6/1990 | Hultquist et al. | 55/270 |
| 5,460,636 | 10/1995 | Harada et al. | 55/270 |
| 5,563,330 | 10/1996 | Kimmig | 55/270 |
| 5,650,560 | 7/1997 | Troost | 95/226 |

OTHER PUBLICATIONS

"A new technique for gettting oxgen and moisture from gases used in semiconductor processing" Apl. Phys. Left. vol. 41, Issue I pp. 88–89, Jul. 1982.

*Primary Examiner*—Duane S. Smith
*Attorney, Agent, or Firm*—Burns, Doane, Swecker & Mathis, L.L.P.

[57] ABSTRACT

A process to detect metal impurities in a gas or gas mixture including the steps of directing the gas or gas mixture through non-metallic pipings to a sampling device and sampling the gas or gas mixture for metal impurities detection, wherein the sampling device is close to an inlet and/or outlet of a machine employing the gas or gas mixture as a processing gas, the machine being surrounded by a booth containing a gaseous atmosphere which is continuously circulated in the booth, partially renewing said atmosphere continuously, and exhausting excess atmosphere.

23 Claims, 1 Drawing Sheet

METHOD TO DETECT METAL IMPURITIES IN THE SEMICONDUCTOR PROCESS GASES

BACKGROUND OF THE INVENTION

1. Field of the Invention

The invention relates to detection of metal impurities in the semiconductor process gases and more particularly immediately at the inlet/outlet of the semiconductor process machine.

2. Description of the Related Art

Trace metal contamination in the Ultra Large Scale Integration manufacturing process ULSI, causes poor electrical property in the devices. Electrical properties of the integrated circuit can be altered by the presence of metal impurities in the process gases used during the manufacturing process of the integrated circuits, even with impurity level as low as 10 ppb or even 1 ppb. Therefore, it is an aim of the present invention to control the metal impurity levels in the process gases below those levels. As the integration of the semiconductor devices are advanced, the requirement for the metal contamination control will become even stricter.

Various methods are known to detect metal impurities in the process gases. A first method known as the bubbling method consists of bubbling the process gases through pure water or a dilute acid solution to trap metal impurities in it. The water or the acid solution is then analysed by ICPAES (Inductively Coupled Plasma Atomic Emission Spectrometry), ICPMS (Inductively Coupled Plasma Mass Spectrometry), and/or GFAAS (Graphite Furnace Atomic Absorption Spectrometry) after the appropriate solution preparation, knows by the man skilled in the art.

A second method known as the hydrolysis method consists of absorbing the process gas to be analyzed into pure water together with metal impurities in the gas and to analyze the resultant solution by ICPAES (Inductively Coupled Plasma Atomic Emission Spectrometry), ICPMS (Inductively Coupled Plasma Mass Spectrometry), and/or GFAAS (Graphite Furnace Atomic Absorption Spectrometry) after appropriate solution preparation, well known by the man skilled in the art.

A third method known as the filtration method consists of passing the gas through a filter to trap metal impurities in the gas, then washing out the trapped metals into a dilute acid solution, and analyzing the solution by ICPAES (Inductively Coupled Plasma Atomic Emission Spectrometry), ICPMS (Inductively Coupled Plasma Mass Spectrometry), and/or GFAAS (Graphite Furnace Atomic Absorption Spectrometry) after appropriate solution preparation.

These various methods are disclosed for example in Proceedings of Technical Conference in Semicon Europe 1992, <<Metals and dopants analysis in electronic specialty gases>> by Martine Carré, which is incorporated herein by a reference.

Semiconductor manufacturing, such as etching, is made by using pure or diluted gases. These gases are usually provided to the semiconductor manufacturer in cylinders which are installed usually in gas cabinets at a remote location from the reactor where semiconductors are manufactured and gas is provided therein through pipings. Most of the semiconductor process gases are either reactive or corrosive and metal contamination can be introduced not only from the source gas in the cylinder but also from various components in the gas delivery system. Therefore, it is desirable that the metal impurities can be monitored and controlled at the immediate inlet of the process machine or reactor (the point of use) rather than at the exit of the gas cylinder in order to know exactly which quantity of the metallic impurities is introduced in the process machine.

Semiconductor process machines are generally placed in a clean room where workers are present. In a monitoring/controlling process at the point of use, as new devices are introduced in the gas delivery pipings, there is an increased risk of leaks and the safety of the workers in the clean room not including the damage to various process, equipment there, can be very serious.

On the other hand, since the required control level of the metal impurities in the process gases are at least in the order of a few ppb or a few tens of ppb, it is desired to avoid metallic materials in the sampling device as much as possible which may in turn, increase the level of metallic impurities. The problem, if using non metallic sampling device, however, is that it is difficult to obtain sufficient pressure resistance and leak tightness with non-metallic materials.

SUMMARY AND OBJECTS OF THE INVENTION

It is therefore an aim of the present invention to detect the metal impurities in a process gas at the point of use substantially at the inlet of the process machine without additional contamination from the metal impurities sampling device and with sufficient safety.

According to a first aspect of the invention, the gas to be analyzed is sampled at pressure near the atmospheric pressure so as to allow the use of non-metallic materials such as polytetrafluoroethylene material or any other appropriate polymer material in the sampling device with no metallic contamination from the sampling device and with sufficient safety.

According to another aspect of the invention, redundant valves in the inlet and outlet of the sampling device are provided to minimize the potential gas leakage;

According to another aspect of the invention, a plastic booth is provided to cover the sampling device whose air is extracted so as not to contaminate the clean room air in case of gas leakage from the sampling device.

DETAILED DESCRIPTION OF PREFERRED EMBODIMENTS OF THE INVENTION

Figure 1:
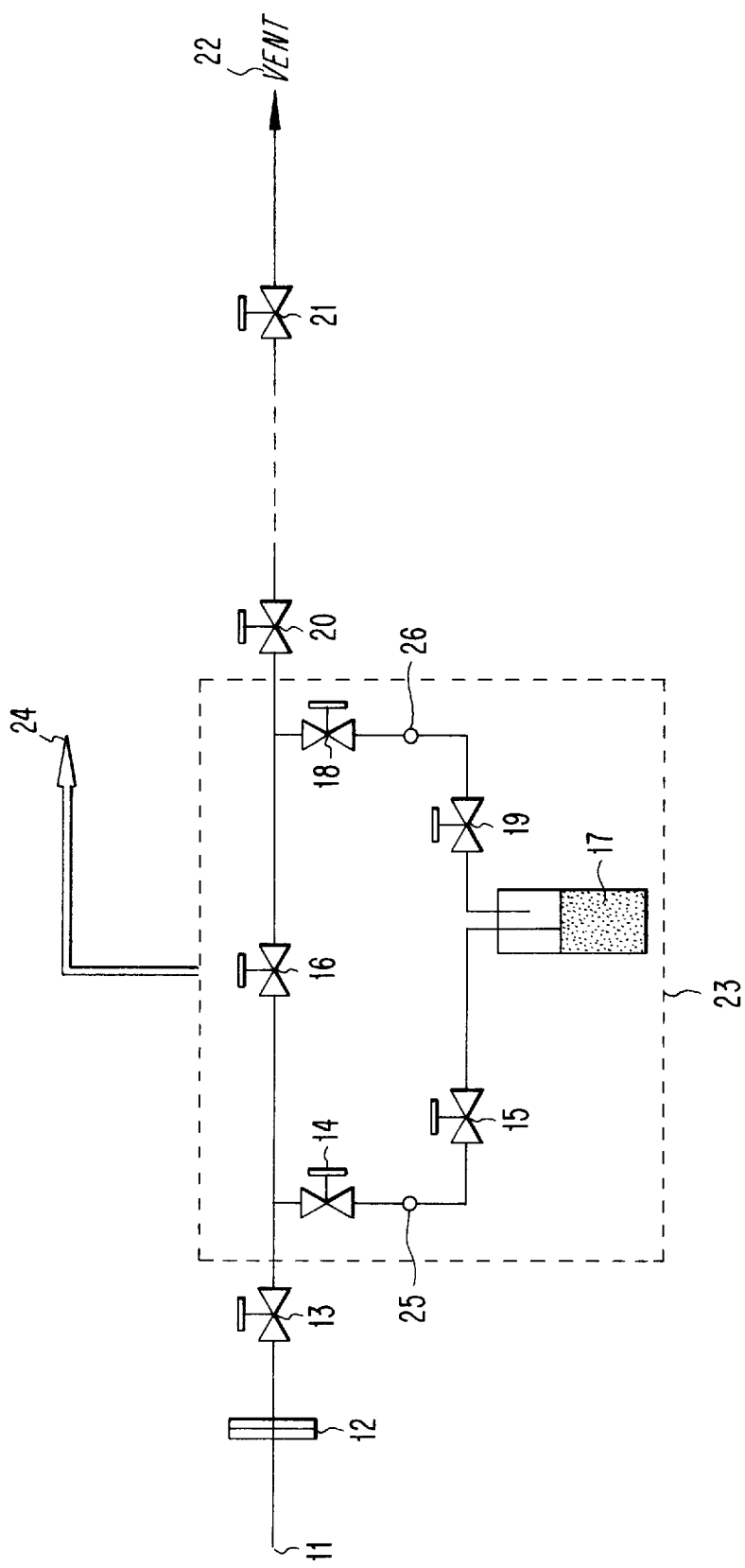
FIG. 1 is an example of a sampling device according to the invention.

On FIG. 1, the various numerals have the following meaning:

11: connection to points to sample the gas near the process machine,
12: orifice or needle valve (if there is no flow controller in the process machine side),
13, 14, 15, 16, 18, 19, 20, 21: valves
17: bubbler or impinger,
22: connection to the abatement system,
23: a plastic booth,
24: exhaust out of the clean room.

A bubbler, an impinger or a filter is alternatively represented by 17 on FIG. 1 according to the selected sampling method. The sampling device of FIG. 1 is connected to the semiconductor process machine at point 11 by an appropriate fitting. The gas flow rate can be controlled by the process machine if it has a controlling device, otherwise an orifice (12) should be installed to control it. The flow rate is determined by considering the typical operational flow rate which is usually between 100 and 1000 sccm, i.e. between 13 and 21.

Before actually sampling the gas, the gas is first circulated (and thereafter discarded) through 11-12-13-16-20-21-22 during at least 5 minutes, and preferably about 60 minutes, to minimize the effect on the sampling results of the contamination due to the connection of the sampling device. During this first step of the process, valves 14 and 18 are closed and valve 16 is open. In a second step of the process, the gas is sampled by closing valve 16 and opening valves 14 and 18. The total sampling volume must be determined by taking into account the basic physical and chemical property of the gas. The maximum sampling volume must be determined by solubility of gases into water and the volume of the water in the impinger or bubbler. If the solubility of the metallic compounds which are expected to exist in the sample gas, is small in the acqueous diluted acid solution in the impinger or bubbler, the sample gas volume must also be determined by the expected contaminant concentration in the sample gas and the volume of the water or diluted acid solution in the impinger or bubbler. The sampling method must be selected among bubbling method, hydrolysis method, and filtration method according to the physical/chemical property of the gas. Bubbling method is applied to gases which show small solubility into water or diluted acid solution although the metallic contaminant in those gases exist as chemical form which can dissolve into water or diluted acid solution. Hydrolysis method is applied to gases which are able to dissolve into water.

When the sampling is completed, valves 15, 19, 14 and 18 are closed and valve 16 is opened. In order to remove the sample gas out of the gas line, said line is purged with filtered $N_2$ gas having a metal impurities content less than about 10 ppt (by weight) and preferably less than 1 ppt by weight). Then the valve 16 is closed and valves 14, 18, 15, 19 are opened to purge the remaining sample gas from the sampling device with the same filtered nitrogen gas. It is preferred to close 15, 19, 14 18 and open 16 in this order. Thereafter, the sampling device is disconnected at point 25 between valves 14 and 15 and that 26 between valves 18 and 19. By doing this post-purging procedure, the contamination of the clean room by the sample gas is minimized.

Valves 14, 16 and 18 can be replaced with a 6-port rotary valve for the same function.

Valve switching procedure must be done quickly so as not to minimize pressure build up in the sampling device and to avoid this pressure to become significantly higher than the atmospheric pressure.

This invention can be used for any gas except gases which react with polymers such as polytetrafluoroethylene which is used in the sampling device of the invention. For example, F2 and $ClF_3$ which react with polytetrafluoroethylene should not be sampled using the invention.

DETAILED EMBODIMENT OF THE INVENTION

EXAMPLE 1

Metals in $N_2$ gas $N_2$ gas is sampled near the process machine which utilises this $N_2$ gas. The sampling flow rate is 250 sccm which is controlled by a mass flow controller built in the machine. The exhaust gas is abated with an abatement system installed with the machine. The sampling is done by bubbling, and the resultant solution is analyzed by ICPMS (Inductively Coupled Plasma Mass Spectrometry) and GFAAS (Graphite Furnace Atomic Absorption Spectrometry). The results are shown in Table 1.

The sampling was done using the sampling kit illustrated on FIG. 1. A 125 ml impinger filled with 100 ml of 1% $HNO_3$ in DI water was set at the point of 17. Valves 14, 15, 19, 18 were closed and 13, 16, 20 and 21 were opened, and the purge of the sample gas $N_2$ were done for 5 minutes. Valves 15 and 19 were opened, and then valve 16 was opened, immediately 14 and 18 were closed. The $N_2$ gas was started to bubble through the DI water in the impinger 17. After the bubbling for 30 minutes, valves 15 and 19 were closed, 14 and 18 were closed, and then immediately valve 16 was opened. In case of $N_2$, there is no risk of leakage of small gas volume remained in the lines between valve 14 and 15, 18 and 19. Therefore no post-purge was applied. At the points of 25 and 26, the impinger was removed from the samplings kit. The solution in the impinger was analyzed by ICPMS (Inductively Coupled Plasma Mass Spectrometry) and GFAAS (Graphite Furnace Atomic Absorption Spectrometry).

In all of the following Tables, units for measured values are "wt.ppb".

TABLE 1

Metals detected in $N_2$ gas coming into the process machine.

| Element | Detection Limit | N2 |
|---------|-----------------|-----|
| Al | 0,11 | Lower than detection limit. |
| Ca | 0,22 | " |
| Co | 0.005 | " |
| Cr | 0.02 | " |
| Cu | 0.02 | " |
| Fe | 0.04 | " |
| K | 0.26 | " |
| Mg | 0.04 | " |
| Mn | 0.01 | " |
| Na | 0.14 | " |
| Ni | 0.03 | 0.12 |
| Pb | 0.005 | 0.008 |
| Zn | 0.01 | 0.05 |

The results are all less than the detection limits except Ni, Pb and Zn. From these results, it can be seen that the $N_2$ gas used in the semiconductor process machine has an excellent purity and that the nitrogen gas delivery system and the sampling device are all very clean.

EXAMPLE 2

Metals in HCl Gas

HCl gas is sampled near the semiconductor process machine after the sampling of $N_2$ in example 1. The sample gas flow rate is 250 sccm which is controlled by a mass flow controller built in the process machine. The exhaust gas is abated with an abatement system installed with the process machine. Sampling is done by hydrolysis, and the resultant solution is analyzed by ICPMS (Inductively Coupled Plasma Mass Spectrometry) and GFAAS (Graphite Furnace Atomic Absorption Spectrometry). The results are summarised in Table 2.

TABLE 2

Metals detected in the HCl gas coming into the process machine.

| Element | Detection Limit | HCl |
| --- | --- | --- |
| Al | 0.04 | 0.94 |
| Ca | 0.37 | below detection limit |
| Co | 0.002 | " |
| Cr | 0.09 | " |
| Cu | 0.01 | " |
| Fe | 0.33 | " |
| K | 0.46 | 0.92 |
| Mg | 0.08 | below detection limit |
| Mn | 0.02 | " |
| Na | 0.06 | " |
| Ni | 0.05 | 0.12 |
| Pb | 0.005 | 0.02 |
| Zn | 0.04 | below detection limit |

Al, K, Ni and Pb are detected from HCl gas used in this particular process machine. Since the cleanliness of the sampling device is proved by the previous $N_2$ analysis, all the detected elements are carried to the process machine by the HCl gas.

EXAMPLE 3

$SiH_4$ Filtration $SiH_4$ gas is sampled near the process machine which utilises $SiH_4$ gas. The sampling flow rate is between 500–3000 sccm which is controlled by a mass flow controller built in the machine. The exhaust gas is abated with an abatement system installed with the machine. Sampling is done by filtration, and the trapped metals are leached into a dilute solution. The resultant solution is analyzed by ICPMS (Inductively Coupled Plasma Atomic Emission Spectrometry) and GFAAS (Graphite Furnace Atomic Absorption Spectrometry). The results are shown in Table 3.

TABLE 3

Metals detected in the $SiH_4$ gas coming into the process machine.

| Element | Detection Limit | amount |
| --- | --- | --- |
| Al | 0.59 | below detection limit |
| As | 0.002 | " |
| B | 0.015 | " |
| Ca | 0.035 | " |
| Cd | 0.001 | 0.046 |
| Co | 0.001 | below detection limit |
| Cr | 0.016 | " |
| Cu | 0.005 | 0.010 |
| Fe | 0.099 | below detection limit |
| K | 0.43 | " |
| Mg | 0.056 | " |
| Mn | 0.001 | " |
| Mo | 0.001 | " |
| Na | 0.148 | " |
| Ni | 0.032 | " |
| P | 0.043 | " |
| Pb | 0.001 | " |
| Sb | 0.001 | " |
| Sn | 0.003 | " |
| Zn | 0.04 | 0.026 |

The result indicates that the sampled $SiH_4$ gas is very clean.

The above examples show that the present method is very sensitive to detect metals in gases.

We claim:

1. A process to detect metal impurities in a gas or gas mixture comprising the steps of directing said gas or gas mixture through non-metallic pipings to a sampling device and sampling the gas or gas mixture for metal impurities detection, wherein said sampling device is close to an inlet and/or outlet of a machine employing said gases or gas mixture as a processing gas, said machine being surrounded by a booth containing a gaseous atmosphere which is continuously circulated in said booth, partially renewing said atmosphere continuously, and exhausting excess atmosphere.

2. The process according to claim 1, wherein said pipings and sampling device comprise polytetrafluoroethylene.

3. The process according to claims 1 or 2, wherein the sampling is carried out at a pressure which is about atmospheric pressure.

4. The process according to claims 1 or 2, further comprising the step of first circulating the gas or gas mixture to be sampled into the pipings and sampling device, then discarding said gas or gas mixture from the pipings and sampling device at least five minutes before actually sampling said gas or gas mixture.

5. The process according to claims 1 or 2, further comprising the step of purging the sampling device with filtered nitrogen having a metal impurities content less than about 10 ppt.

6. The process according to claim 1, wherein said gas or gas mixture is employed in said machine as a processing gas in a semiconductor manufacturing process.

7. The process according to claim 6, wherein said machine is located in a clean room.

8. The process according to claim 7, wherein said excess atmosphere is exhausted outside said clean room.

9. A process for detecting metal impurities in a gas or gas mixture used as a process gas in a machine having an inlet and an outlet for said gas or gas mixture comprising the steps of:

(i) removing said gas or gas mixture, through a non-metallic piping, from a point close to at least one of the inlet and outlet of said machine;

(ii) directing said gas or gas mixture through said non-metallic piping to a sampling device for further analysis and detection of metal impurities, said sampling device being enclosed in a gaseous atmosphere which is isolated from said machine and continuously circulated; and (iii) continuously partially removing an excess of said gaseous atmosphere enclosing said sampling device, said removed atmosphere being exhausted in isolation from said machine.

10. The process of claim 9, wherein said machine is a semiconductor manufacturing process machine.

11. The process of claim 10, wherein said machine is located in a clean room.

12. The process of claim 11 wherein the gaseous atmosphere removed in step (iii) is removed outside said clean room.

13. The process of claim 9 wherein said sampling device is surrounded by a booth which encloses said gaseous atmosphere.

14. The process of claim 9 wherein said non-metallic piping comprises polytetrafluoroethylene.

15. The process of claim 9, wherein said sampling device comprises polytetrafluoroethylene.

16. The process of claim 9, wherein said gas or gas mixture directed to said sampling device is at about atmospheric pressure.

17. The process of claim 9 further comprising the steps of:
first circulating said gas or gas mixture into said piping and sampling device; and
then discarding said first gas or gas mixture for at least five minutes before actually analyzing said gas or gas mixture.

18. The process according to claim 9, further comprising the step of purging said sampling device with filtered nitrogen having a content of metal impurities of less than about 10 ppt.

19. The process of claim 1, wherein sampling the gas or gas mixture for metal impurities detection comprises bubbling the gas in water or a diluted acid solution.

20. The process of claim 1, wherein sampling the gas or gas mixture for metal impurities detection comprises hydrolyzing the gas.

21. The process of claim 1, wherein sampling the gas or gas mixture for metal impurities detection comprises filtrating the gas or gas mixture to trap metal impurities present in the gas or gas mixture and forming a dilute solution comprising the trapped metal impurities.

22. The process of claim 1, wherein sampling the gas or gas mixture for metal impurities detection comprises analysis by Inductively Coupled Plasma Atomic Emission Spectrometry (ICPMS).

23. The process of claim 1, wherein sampling the gas or gas mixture for metal impurities detection comprises analysis by Graphite Furnace Atomic Emission Spectrometry (GFAAS).

* * * * *